United States Patent [19]

McCombie et al.

[11] Patent Number: 4,504,485

[45] Date of Patent: Mar. 12, 1985

[54] 5R,6S,8R-6-(1-HYDROXYETHYL)-2-(2-CARBAMOYLOXYETHYLTHIO)-PENEM-3-CARBOXYLIC ACID

[75] Inventors: Stuart W. McCombie, West Orange; Ashit K. Ganguly, Upper Montclair; Viyyoor M. Girijavallabhan, Parsippany, all of N.J.

[73] Assignee: Schering Corporation, Kenilworth, N.J.

[21] Appl. No.: 481,551

[22] Filed: Apr. 4, 1983

[51] Int. Cl.³ .................. C07D 499/00; A61K 31/425
[52] U.S. Cl. .............................. 514/192; 260/245.2 R; 260/245.2 T
[58] Field of Search ................. 260/245.2 R, 245.2 T; 424/270, 271

[56] References Cited

U.S. PATENT DOCUMENTS 4,260,618  4/1981  Christensen et al. ........ 260/245.2 R

FOREIGN PATENT DOCUMENTS 0176988  10/1982  Japan.
0043978  3/1983  Japan.

*Primary Examiner*—Nicholas S. Rizzo
*Attorney, Agent, or Firm*—Gerald S. Rosen

[57] ABSTRACT

There is disclosed the antibacterial 5R,6S,8R-6-(1-hydroxyethyl)-2-(2-carbamoyloxyethylthio)-penem-3-carboxylic acid, its pharmaceutically acceptable salts and metabolizable esters as well as compositions containing them and methods for their use, preferably the sodium salt for parenteral administration.

7 Claims, No Drawings

5R,6S,8R-6-(1-HYDROXYETHYL)-2-(2-CARBAMOYLOXYETHYLTHIO)-PENEM-3-CARBOXYLIC ACID

BACKGROUND OF THE INVENTION

This invention relates to 5R,6S,8R-6-(1-hydroxyethyl)-2-(2-carbamoyloxyethylthio)-penem-3-carboxylic acid and its pharmaceutically acceptable salts and metabolizable esters, which compounds possess potent anti-bacterial activity.

There is a continuing need for new antibacterial agents because continued extensive use of effective antibacterials gives rise to resistant strains of pathogens.

SUMMARY OF THE INVENTION 5R,6S,8R-6-(1-hydroxyethyl)-2-(2-carbamoyloxyethylthio)-penem-3-carboxylic acid and its pharmaceutically acceptable salts and metabolizable esters possess antibacterial activity against both gram-negative and gram-positive bacteria.

DETAILED DESCRIPTION

When tested in standardized microbiological assays, the compounds of this invention are active against such gram-positive organisms as *Staphylococcus epidermis* and *Bacillus subtilis*, and such gram-negative organisms as *E. coli* and *Salmonella*, at test levels of 0.6 to 2.0 micrograms/ml. Additionally, they show activity against organisms which produce beta-lactamases, e.g., penicillinase and cephalosporinase, indicating a resistance against these enzymes. For instance, the sodium salt of 5R,6S,8R-6-(1-hydroxyethyl-2-(2-carbamoyloxyethylthio)penem-3-carboxylic acid is active against *E. coli* 74081501 (a beta-lactamase producing organism) at a test level of 0.1250 microgram/ml.

The compounds of this invention exhibit low protein binding and their metabolites have little or no unpleasant odor.

As antibacterial agents, the compounds of this invention are conventionally formulated for oral, parenteral, topical and transdermal use preferably parenteral. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents, enzyme inhibitors and/or absorption enhancers.

For the preferred parenteral administration, they may be formulated into solutions or suspensions. Typical topical formulations are those such as lotions, creams, ointments, sprays, and mechanical delivery devices, e.g., transdermal. For oral administration, the compounds of this invention are typically formulated in the form of tablets, capsules, elixirs, or the like.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene gylcol polymers; betacyclodextrin; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, thickening, suspending, dispensing, emulsifying, wetting, stabilizing and buffering agents.

The dosage of a compound of this invention which is administered is in accordance with the judgement of the attending clinician and depends upon a variety of factors, i.e., the age and weight of the individual being treated, the mode of administration, and the type and severity of the bacterial infection being prevented or reduced. Typically, the dosage administered per day will be in the range of from about 25 to 160 mg/kg and preferably from about 50 to 100 mg/kg in divided dosages. Typically, the dosage will be administered in dosage units containing convenient amounts, for example, 0.250, 0.500, 1 or 2 gms of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cyloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine (β-methylamino-α-phenyl-benzene ethanol) and N-alkylpiperidine.

"Pharmaceutically acceptable metabolizable esters" means physiologically cleavable esters, i.e., those esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Thus, salts of the compound can be formed, for example, by treating it with metal compounds such as alkali metal salts of suitable carboxylic acids, or with ammonia or a suitable organic amine, wherein preferably stoichiometric amounts or only a small-excess of the salt-forming agent is used. The esters are preparable in a manner analogous to the preparation of the corresponding esters of penicillins and cephalosporins.

The compounds of this invention can be prepared by several methods as follows:

(a) From the allyl ester of 5R,6S,8R-6-(1-protected hydroxyethyl)-2-(2-hydroxyethylthio)-penem-3-carboxylic acid (prepared as disclosed in European Patent Application No. 80810004.4, published July 23, 1980 as No. 0013662) by reaction with potassium cyanate and trifluoroacetic acid in methylene dichloride followed by deprotection of the hydroxy group and removal of the allyl group to form an alkali metal salt, preferably the sodium salt. Treatment of the salt with, e.g., tartaric acid, converts the salt to the carboxylic acid; or (b) Activating the allyl ester of 5R,6S,8R-6-(1-hydroxyethyl)-2-(2-ethylthio)penem-3-carboxylate, prepared as disclosed in European Patent Application No. 80810004.4, published July 23, 1980 as No. 0013662) to the sulfoxide and displacement at the 2-position with 2-(carbamoyloxy)-ethanethiol, followed by removal of the allyl group to form an alkali metal salt, preferably the sodium salt. Treatment of the salt with, e.g., tartaric acid, converts the salt to the carboxylic acid.

The following examples illustrate the preparation of the compounds and compositions of this invention.

EXAMPLE 1

ALLYL-(5R,6S,8R)-2-(2-CARBAMOYLOXYE-THYLTHIO)-6-(1-[TRICHLOROETHOXYCARBONYLOXY]-ETHYL)-PENEM-3-CARBOXYLATE

Stir at 0°–5° C. a mixture of 0.80 g powdered potassium cyanate and 1.1 g of allyl-(5R,6S,8R)-6-(1-[trichlorethoxycarbonyloxy]-ethyl)-2-(2-hydroxyethylthio)-penem-3-carboxylate in 5 ml $CH_2Cl_2$ and add dropwise 1.1 g trifluoroacetic acid. Stir the mixture at 0°–5° C. for one-half hour and 6 hours at 25° C. Work up in $CH_2Cl_2$ aqueous $NaHCO_3$, then dry, evaporate and chromatograph the organic phase on silica gel in ether-$CH_2Cl_2$ to yield the title compound as a yellow oil.

IR spectrum ($CH_2Cl_2$ solution) $\nu$ max 3500, 1795, 1750 and 1700 cm$^{-1}$. NMR ($CDCl_3$): $\delta$ 1.53(d,3,J=7), 3.22(m,2), 3.90(dd,1,J=1.5 and 8.5), 4.32(d,2,J=7), 4.79(s,2), 4.5–5.0 (m,4), 5.05–5.55(m,2), 5.66(d,1,J=1.5) and 5.7–6.2(m,1).

EXAMPLE 2

ALLYL-(5R,6S,8R-(2-(2-CARBAMOYLOXYE-THYLTHIO)-6-(1-HYDROXYETHYL)-PENEM-3-CARBOXYLATE

Stir a mixture of 0.47 g of the product of Example 1, 0.45 g zinc dust, 0.6 ml. acetic acid, 0.6 ml. water and 6 ml. tetrahydrofuran (THF) for two hours at 25° C. Work up in ethylacetate-$H_2O$, dry and evaporate the organic phase, then subject it to thin layer chromatography (25% ether-dichloromethane) to yield the title compound as a pale yellow foam.

IR spectrum ($CH_2Cl_2$) $\nu$ max 3400, 1790, 1710 and 1690 cm$^{-1}$; H NMR (DMSO-$d_6$): $\delta$ 1.13(d,2,J=7), 3.20(m,2), 3.85(m,2), 4.14(t,2,J=7), 5.64(m,2), 5.1–5.5 (m,2), 5.71 (d,1,J=1.5), 5.7–6.2(m.1) and 6.55 (br.s, 2, exch. by $D_2O$).

EXAMPLE 3

ALLYL-(5R,6S,8R)-2-(ETHANESULFINYL)-6-(1-HYDROXYETHYL)-PENEM-3-CARBOXYLATE

Stir at 0°–5° C. a solution of allyl-(5R,6S,8R)-ethylthio-6-(1-hydroxyethyl)-penem-3-carboxylate (31.5 g) in ethyl acetate (200 ml) and dichloromethane (100 ml) and add over 0.5 hours a solution of m-chloroperoxybenzoic acid (80–85%; 22 g) in ethyl acetate (120 ml). After a further 0.5 hours, add the solution to a stirred mixture of ethyl acetate (150 ml), water (125 ml) and sodium bicarbonate (15 g), and stir rapidly for 15 mins. Dry the organic phase over $MgSO_4$, evaporate and chromatograph rapidly on silica gel, elute 1:1 hexane-ethyl acetate then pure ethyl acetate. Evaporate the product fractions and pump the residue at high vacuum to give the title compound as a thick yellow oil.

NMR ($CDCl_3$): $\delta$ 1.2–1.6 (m, 6H), 3.0–3.35 (m, 2H), 3.38 (br.s, 1H, exch by $D_2O$), 3.83 (m, 1H), 4.18 (m, 1H), 4.75 (br.d, J=6.5 Hz), 5.2–5.6 (m, 2H), 5.73 and 5.89 (both d, J=1.5 Hz, total 1H) and 5.8–6.2 (m, 1H).

EXAMPLE 4

ALLYL-(5R,6S,8R)-2-(2-CARBAMOYLOXYE-THYLTHIO)-6-(1-HYDROXYETHYL)-PENEM-3-CARBOXYLATE

Stir a mixture of 1.8 g of 2-(carbamoyloxy)-ethanethiol, 4.4 g of the product of Example 3 and 80 ml of dichloromethane for 1 hour at 0°–5° C. while adding 1.6 ml. of diisopropylethylamine. Chromatograph the mixture on silica gel, eluting with increasing concentrations (5–15%) of acetone in $CH_2Cl_2$. Evaporate the pure fractions to yield the title compound as a pale yellow solid, identical to the product of Example 2.

EXAMPLE 5

SODIUM (5R,6S,8R)-2-(2-CARBAMOYLOXYETHYLTHIO)-6-(1-HYDROXYETHYL)-PENEM-3-CARBOXYLATE

Stir under nitrogen at 25° C. a mixture of 1.2 g of the compound produced in Examples 2 and 4, 0.55 g of 2-ethylhexanoate, 0.12 g triphenylphosphine and 40 ml. dry tetrahydrofuran. Add 0.12 g tetrakis-(triphenylphosphine)-palladium, then stir for 2 hours and add 100 ml ether, centrifuge and wash with ethyl acetate. Dissolve the resulting salt in water and chromatograph on 10 g of reverse-phase C-18 silica, eluting with water. Combine pure fractions and lyophilize to obtain the product as a pale yellow powder.

IR(Nujol mull) $\nu$ max 3500, 1775, 1700 and 1650–1600 cm$^{-1}$.

The compounds of this invention can also be prepared by reacting 2-(carbamoyloxy)ethanyliodide with allyl (5R,6S,8R)-2-thioxo-6-(1-hydroxyethyl)penam-3-carboxylate (prepared and disclosed in commonly assigned copending application Ser. No. 445,295, filed Nov. 29, 1982) in a basic medium then removing the allyl group as described in Example 5 herein.

The compounds of this invention can also be prepared by the procedures described in U.S. Pat. No. 4,347,183, utilizing the appropriate intermediates to make the compound of Example 1 herein, then following the procedures of Examples 2 and 5 herein.

In the following examples, the Active Ingredient is sodium 5R,6S,8R-6-(1-hydroxyethyl)-2-(2-carbamoyloxyethylthio)-penem-3-carboxylate.

EXAMPLE 6

| Injectable Powder: (per vial) | | | |
|---|---|---|---|
| | g/vial | g/vial | g/vial |
| Active Ingredient Sterile Powder | 00.5 | 1.0 | 2.0 |

Add sterile water for injection or bacteriostatic water for injection, USP for reconstitution.

EXAMPLE 7

| Injectable Solution: | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65–70° C.
2. Cool to 25–35° C. Charge and dissolve the sodium bisulfate, disodium edetate and sodium sulfate.
3. Charge and dissolve Active Ingredient.
4. Bring the solution to final volume by adding water for injection.
5. Filter the solution through 0.22 micron membrane and fill into appropriate containers.
6. Terminally sterilize the units by autoclaving.

EXAMPLE 8

| Injectable Powder: (lyophilized powder, per vial) | | |
|---|---|---|
| | g/vial | g/vial |
| Active Ingredient | 1.0 | 2.0 |
| Sodium Citrate | 0.05 | 0.10 |

Add sterile water for injection or bacteriostatic water for injection for reconstitution.

We claim:
1. 5R,6S,8R-6-(1-hydroxyethyl)-2-(2-carbamoyloxyethylthio)penem-3-carboxylic acid and the pharmaceutically acceptable salts and metabolizable esters thereof.
2. The compound of claim 1 wherein the pharmaceutically acceptable salt is an alkali metal salt.
3. The compound of claim 2 wherein the alkali metal salt is sodium.
4. An antibacterially effective pharmaceutical composition comprising an antibacterially effective amount of a compound of claim 1 in admixture with a pharmaceutically acceptable carrier.
5. A composition according to claim 4 adapted for parenteral administration.
6. A method of treating or preventing susceptible bacterial infections which comprises administering to a host in need of such treatment or prevention a compound of claim 1 or a pharmaceutical composition thereof in an amount sufficient to treat or prevent such infection.
7. A method according to claim 6 wherein the route of administration is parenteral.

* * * * *